United States Patent
Kleemann

(10) Patent No.: US 7,375,138 B2
(45) Date of Patent: May 20, 2008

(54) PENTAFLUOROSULFANYLBENZOYL-GUANIDINES, PROCESSES FOR THEIR PREPARATION, THEIR USE AS MEDICAMENTS OR DIAGNOSTIC AIDS, AND MEDICAMENTS COMPRISING THEM

(75) Inventor: Heinz-Werner Kleemann, Bischofsheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 515 days.

(21) Appl. No.: 10/429,810

(22) Filed: May 5, 2003

(65) Prior Publication Data
US 2003/0216476 A1 Nov. 20, 2003

Related U.S. Application Data

(60) Provisional application No. 60/412,096, filed on Sep. 19, 2002.

(30) Foreign Application Priority Data
May 18, 2002 (DE) ................ 102 22 192

(51) Int. Cl.
*A61K 31/65* (2006.01)
*C07C 309/00* (2006.01)
(52) U.S. Cl. .................. 514/618; 562/824
(58) Field of Classification Search .............. None
See application file for complete search history.

(56) References Cited

U.S. PATENT DOCUMENTS

| | | |
|---|---|---|
| 5,571,842 A | 11/1996 | Kleemann et al. |
| 5,747,539 A | 5/1998 | Dorsch et al. |
| 5,866,610 A | 2/1999 | Lang |
| 6,114,393 A | 9/2000 | Lang |
| 6,156,800 A | 12/2000 | Weichert et al. |
| 6,348,476 B1 | 2/2002 | Scholz et al. |
| 6,420,430 B1 | 7/2002 | Linz |
| 6,462,024 B1 | 10/2002 | Lang |

OTHER PUBLICATIONS

"NIH Heart Disease & Stroke Research: Fact Sheet" (American Heart Association, 2004.*
"Cardiovascular Disease: Treatment for Stroke", Stanford Hospital & Clinics, 2003.*
"Acute Congestive Heart Failure", Thomas N. Levin, Postgraduate Medicine, vol. 101, No. 1, 1997.*
Cecil Textbook of Medicine, 20th Edition, 1987.*
Angew STAAB, Syntheses Using Heterocyclic Amides (Azolides) [*], Chem. Int. Ed. Engl, 1, 251-367.
J. March, Aliphatic Nucleophilic Substitution, Advanced Organic Chemistry, 3rd Edition, John Wiley & Sons, 1985, p. 350.
Konig W. et al., Perchloric Acid In Peptide Chemistry, Peptides, (1990), Proc. European Peptide Symp., 21st (1991), pp. 143-145.
Sheppard William A., Arylsulfur Pentafluorides, Journal of the American Chemical Society; vol. 84; No. 16; (Aug. 20, 1962); pp. 3064-3072.

* cited by examiner

*Primary Examiner*—Brian Kwon
(74) *Attorney, Agent, or Firm*—Raymond S. Parker, III; Robert J. Kajubi

(57) ABSTRACT

Pentafluorosulfanylbenzoylguanidines of the formula I and II

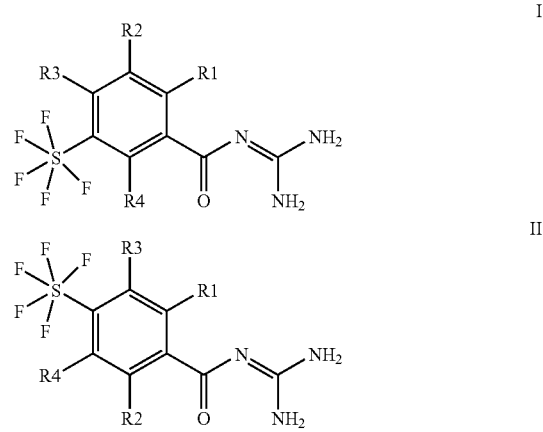

in which R1 to R4 have the meanings stated in the claims, are suitable as antiarrhythmic medicaments with a cardioprotective component for the prophylaxis of infarction and treatment of infarction and for the treatment of angina pectoris. They also inhibit preventively the pathophysiological processes associated with the development of ischemia-induced damage, especially in the triggering of ischemia-induced cardiac arrhythmias.

3 Claims, No Drawings

PENTAFLUOROSULFANYLBENZOYL-GUANIDINES, PROCESSES FOR THEIR PREPARATION, THEIR USE AS MEDICAMENTS OR DIAGNOSTIC AIDS, AND MEDICAMENTS COMPRISING THEM

This application claims the benefit of U.S. Provisional Application No. 60/412,096, filed Sep. 19, 2002, incorporated herein by reference.

The invention relates to pentafluorosulfanylbenzoylguanidines of the formula I or II

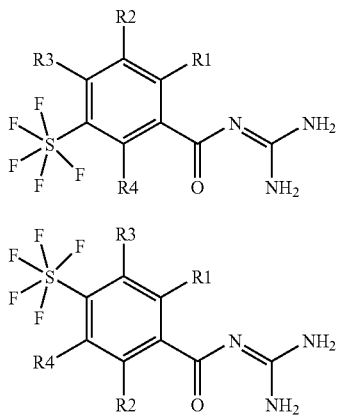

in which

R1 is hydrogen, alkyl having 1, 2, 3 or 4 carbon atoms, alkoxy having 1, 2, 3 or 4 carbon atoms, F, Cl, Br, I, CN, NR10R11, $-O_p-(CH_2)_n-(CF_2)_o-CF_3$ or $-(SO_m)_q-(CH_2)_r-(CF_2)_s-CF_3$;

R10 and R11 are, independently of one another, hydrogen, alkyl having 1, 2, 3 or 4 carbon atoms or $-CH_2-CF_3$;

m is zero, 1 or 2 n, o, p, q, r and s are, independently of one another, zero or 1;

R2 is hydrogen, F, Cl, Br, I, $-CN$, $-SO_2CH_3$, $-(SO_h)_z-(CH_2)_k-(CF_2)_{l-CF3}$, alkyl having 1, 2, 3, 4, 5 or 6 carbon atoms, cycloalkyl having 3, 4, 5, 6, 7 or 8 carbon atoms, in which 1, 2, 3 or 4 hydrogen atoms may be replaced by fluorine atoms;

h is zero, 1 or 2;
z is zero or 1;
k is zero, 1, 2, 3 or 4;
l is zero or 1;

or

R2 is $-(CH_2)_t$-phenyl or $-O$-phenyl, in which each phenyl is unsubstituted or substituted by 1, 2 or 3 radicals selected from the group consisting of F, Cl, Br, I, $-O_u-(CH_2)_v-CF_3$, alkoxy having 1, 2, 3 or 4 carbon atoms, alkyl having 1, 2, 3 or 4 carbon atoms and $-SO_2CH_3$;

t is zero, 1, 2, 3 or 4;
u is zero or 1;
v is zero, 1, 2 or 3;

or

R2 is $-(CH_2)_w$-heteroaryl, in which heteroaryl is unsubstituted or substituted by 1, 2 or 3 radicals selected from the group consisting of F, Cl, Br, I, $-O_x-(CH_2)_y-CF_3$, alkoxy having 1, 2, 3 or 4 carbon atoms and alkyl having 1, 2, 3 or 4 carbon atoms, $-SO_2CH_3$;

w is zero, 1, 2, 3 or 4;
x is zero or 1;
y is zero, 1, 2 or 3;

R3 and R4 are, independently of one another, hydrogen or F;

and the pharmaceutically acceptable salts thereof.

Preference is given to compounds of the formula I or II, in which the meanings are:

R1 hydrogen, alkyl having 1, 2, 3 or 4 carbon atoms, alkoxy having 1, 2, 3 or 4 carbon atoms, F, Cl, NR10R11, $-O-CH_2-CF_3$ or $SO_m(CH_2)_r-CF_3$;

R10 and R11 independently of one another hydrogen, alkyl having 1, 2, 3 or 4 carbon atoms or $-CH_2-CF_3$;

m zero, 1 or 2;
r zero or 1;

R2 hydrogen, F, Cl, $-SO_2CH_3$, $-(SO_h)_z-(CH_2)_k-CF_3$, alkyl having 1, 2, 3 or 4 carbon atoms, cycloalkyl having 3, 4, 5, 6 or 7 carbon atoms, in which 1, 2, 3 or 4 hydrogen atoms may be replaced by fluorine atoms;

h zero, 1 or 2;
z zero or 1;
k zero, 1, 2, 3 or 4;

or

R2 phenyl or $-O$-phenyl, which is unsubstituted or substituted by 1 or 2 radicals selected from the group consisting of F, Cl, $-O_u-(CH_2)_v-CF_3$, methoxy, ethoxy, alkyl having 1, 2, 3 or 4 carbon atoms and $-SO_2CH_3$;

u zero or 1;
v zero, 1, 2 or 3;

or

R2 heteroaryl, which is unsubstituted or substituted by 1 or 2 radicals selected from the group consisting of F, Cl, $-O_x-(CH_2)_y-CF_3$, methoxy, ethoxy, alkyl having 1, 2, 3 or 4 carbon atoms and $-SO_2CH_3$;

x zero or 1;
y zero, 1, 2 or 3;

R3 and R4 independently of one another hydrogen or F;

and the pharmaceutically acceptable salts thereof.

Particular preference is given to compounds of the formula I or II, in which the meanings are:

R1 hydrogen, alkyl having 1, 2, 3 or 4 carbon atoms, methoxy, ethoxy, F, Cl, NR10R11, $-O-CH_2-CF_3$ or $-SO_m-(CH_2)_r-CF_3$;

R10 and R11 independently of one another hydrogen, alkyl having 1, 2, 3 or 4 carbon atoms or $-CH_2-CF_3$;

m zero, 1 or 2;
r zero or 1;

R2 hydrogen, F, Cl, $-SO_2CH_3$, $-(SO_h)_z-(CH_2)_k-CF_3$, alkyl having 1, 2, 3 or 4 carbon atoms, cycloalkyl having 3, 4, 5, 6 or 7 carbon atoms, in which 1, 2, 3 or 4 hydrogen atoms may be replaced by fluorine atoms;

h zero or 2;
z zero or 1;
k zero or 1;

or

R2 phenyl or $-O$-phenyl, which is unsubstituted or substituted by 1 or 2 radicals selected from the group consisting of F, Cl, $-O-(CH_2)_v-CF_3$, methoxy, ethoxy, alkyl having 1, 2, 3 or 4 carbon atoms and $-SO_2CH_3$;

v zero, 1, 2 or 3;

or

R2 heteroaryl, which is unsubstituted or substituted by 1 or 2 radicals selected from the group consisting of F, Cl, —O—(CH$_2$)$_y$—CF$_3$, methoxy, ethoxy, alkyl having 1, 2, 3 or 4 carbon atoms and —SO$_2$CH$_3$;

y zero, 1, 2 or 3;

R3 and R4 hydrogen;

and the pharmaceutically acceptable salts thereof.

It is specifically preferred in the compounds of the formula I and II for R1 to be hydrogen, alkyl having 1, 2, 3 or 4 carbon atoms, F or Cl. It is also specifically preferred in the compounds of the formula I and/or II for R2 to be hydrogen, alkyl having 1, 2, 3 or 4 carbon atoms, F, Cl or —O-phenyl which is unsubstituted or substituted as indicated.

If the substituents R1 to R4 contain one or more centers of asymmetry, these may independently of one another have both the S and the R configuration. The compounds may be in the form of optical isomers, of diastereomers, of racemates or of mixtures thereof.

The present invention encompasses all tautomeric forms of the compounds of the formula I and II.

Alkyl radicals may be straight-chain or branched. This also applies if they carry substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl. Preferred alkyl radicals are methyl, ethyl, n-propyl and isopropyl. One or more, for example 1, 2, 3, 4 or 5, hydrogen atoms in alkyl radicals may be replaced by fluorine atoms. Examples of such fluoroalkyl radicals are trifluoromethyl, 2,2,2-trifluoroethyl and pentafluoroethyl. Substituted alkyl radicals may be substituted in any positions.

Examples of cycloalkyl radicals are cyclopropyl, cyclobutyl, cyclopentyl, cyclohexyl, cycloheptyl or cyclooctyl. One or more, for example 1, 2, 3 or 4, hydrogen atoms in cycloalkyl radicals may be replaced by fluorine atoms. Substituted cycloalkyl radicals may be substituted in any positions.

Phenyl radicals may be unsubstituted or be substituted one or more times, for example once, twice or three times, by identical or different radicals. If a phenyl radical is substituted, it preferably has one or two identical or different substituents. This likewise applies to substituted phenyl radicals in groups such as, for example, phenylalkyl or phenyloxy. The substituent in monosubstituted phenyl radicals may be in position 2, position 3 or position 4. Disubstituted phenyl may be substituted in the 2,3 position, 2,4 position, 2,5 position, 2,6 position, 3,4 position or 3,5 position. The substituents in trisubstituted phenyl radicals may be in the 2,3,4 position, 2,3,5 position, 2,4,5 position, 2,4,6 position, 2,3,6 position or 3,4,5 position.

Heteroaryl radicals are aromatic ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position. Heteroaryl radicals may be unsubstituted or be substituted one or more times, for example once, twice or three times, by identical or different radicals. This applies likewise to heteroaryl radicals such as, for example, in the radical heteroarylalkyl. Examples of heteroaryl are furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

Heteroaryl radicals are, in particular, 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 1-, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also emcompassed are the corresponding N-oxides of these compounds, i.e. for example 2-, 3- or 4-pyridyl 1-oxide.

Particularly preferred heteroaromatic radicals are 2- or 3-thienyl, 2- or 3-furyl, 1-, 2- or 3-pyrrolyl, 1-, 2-, 4- or 5-imidazolyl, 2-, 3-, 4-, 5-, 6-, 7- or 8-quinolyl, 1-, 3-, 4- or 5-pyrazolyl, 2-, 3- or 4-pyridyl, 2- or 3-pyrazinyl, 2-, 4-, 5- or 6-pyrimidinyl and 3- or 4-pyridazinyl.

The invention further relates to a process for preparing a compound of the formula I and II and/or the pharmaceutically acceptable salts thereof, which comprises reacting a compound of the formula III or IV

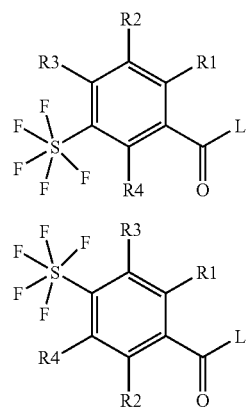

in which R1 to R4 have the stated meaning, and L is a leaving group which can easily undergo nucleophilic substitution, with guanidine.

The activated acid derivatives of the formula III and IV in which L is an alkoxy, preferably a methoxy, group, a phenoxy group, phenylthio, methylthio, 2-pyridylthio group, a nitrogen heterocycle, preferably 1-imidazolyl, are advantageously obtained in a manner known per se from the underlying carbonyl chlorides (formula III, IV; L=Cl), which in turn can themselves be prepared in a known manner from the underlying carboxylic acids (formula III, IV; L=OH), for example using thionyl chloride. Besides the carbonyl chlorides of the formula III and IV (L=Cl) it is also possible to prepare other activated acid derivatives of the formula III and IV in a manner known per se directly from the underlying benzoic acids (formula III, IV; L=OH), such as the methyl esters of the formula III and IV with L=OCH$_3$ by treatment with gaseous HCl in methanol, the imidazolides of the formula III and IV by treatment with carbonyldiimidazole [L=1-imidazolyl, Staab, Angew. Chem. Int. Ed. Engl. 1, 351-367 (1962)], the mixed anhydrides of the formula III and IV with Cl—COOC$_2$H$_5$ or tosyl chloride in the presence of triethylamine in an inert solvent, as activations of benzoic acids with dicyclohexylcarbodiimide (DCC) or with O-[(cyano(ethoxycarbonyl)-methylene)amino]-1,1,3,3-tetramethyluronium tetrafluoroborate ("TOTU") [Proceedings of the 21. European Peptide Symposium, Peptides 1990, Editors E. Giralt and D. Andreu, Escom, Leiden, 1991] are also possible. A number of suitable methods for preparing activated carboxylic acid derivatives of the formula III and IV are indicated in J. March, Advanced Organic Chemistry, third edition (John Wiley & Sons, 1985, page 350), indicating source literature.

Reaction of an activated carboxylic acid derivative of the formula III and IV with guanidine preferably takes place in a manner known per se in a protic or aprotic polar but inert organic solvent. Those which have proved suitable for the reaction of the methyl benzoates (III, IV; L=OCH$_3$) with guanidine are methanol, isopropanol or THF from 20° C. to the boiling point of these solvents. Most reactions of compounds III and IV with salt-free guanidine have advantageously been carried out in aprotic inert solvents such as THF, dimethoxyethane, dioxane. However, it is also possible to use water in the presence of a base such as, for example, NaOH as solvent in the reaction of III and IV with guanidine.

If L is Cl, it is advantageous to add an acid scavenger, for example in the form of excess guanidine, to bind the hydrohalic acid.

The invention also includes precursors of the formula V

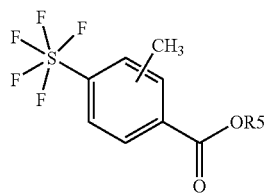

with R5 equal to hydrogen or (C$_1$-C$_4$)-alkyl, in which the methyl group may be in position 2 or position 3 of the aromatic ring.

Pentafluorosulfanylbenzoylguanidines I and II are generally weak bases and are able to bind acids to form salts. Suitable acid addition salts are salts of all pharmacologically acceptable acids, for example halides, in particular hydrochlorides, lactates, sulfates, citrates, tartrates, acetates, phosphates, methylsulfonates, p-toluenesulfonates.

The compounds I and II are substituted acylguanidines and inhibit the cellular sodium-proton antiporter (Na$^+$/H$^+$ exchanger, NHE).

Compared with known compounds, the compounds of the invention are distinguished by an extremely high activity in the inhibition of Na$^+$/H$^+$ exchange, and by improved ADMET properties. The xenobiotic structure (in particular the introduction of the rather "unnatural/manmade" SF$_5$ substituents) impedes the possibility of metabolic attack. This leads inter alia to longer S9 stabilities (liver stabilities, stability to enzymatic attack) and a longer half-life in vivo. This involves no significant influence on the absorption characteristics, and the high bioavailability of the acylguanidines is retained.

In contrast to some acylguanidines described in the literature, the compounds of the formula I and/or II described herein and/or their pharmaceutically acceptable salts show no unwanted and disadvantageous saluretic properties Because of the NHE-inhibitory properties, the compounds of the formula I and/or II and/or the pharmaceutically acceptable salts thereof are suitable for the prevention and treatment of diseases caused by activation of or activated NHE, and of diseases caused secondarily by the NHE-related damage.

Since NHE inhibitors predominantly act via their effect on cellular pH regulation, they can generally be combined beneficially with other compounds which regulate the intracellular pH, with suitable combination partners being inhibitors of the carbonate dehydratase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

The use of the compounds of the invention relates to the prevention and treatment of acute and chronic diseases in veterinary and human medicine.

Thus, the NHE inhibitors of the invention are suitable for the treatment of diseases caused by ischemia and by reperfusion.

The compounds described herein are suitable because of their pharmacological properties as antiarrhythmic medicaments.

Owing to their cardioprotective component, the NHE inhibitors of the formula I and/or II and/or the pharmaceutically acceptable salts thereof are outstandingly suitable for infarction prophylaxis and infarction treatment and for the treatment of angina pectoris, in which cases they also preventively inhibit or greatly reduce the pathophysiological processes associated with the development of ischemia-induced damage, in particular in the triggering of ischemia-induced cardiac arrhythmias. Because of their protective effects against pathological hypoxic and ischemic situations, the compounds of the formula I and/or II and/or the pharmaceutically acceptable salts thereof used according to the invention can, because of inhibition of the cellular Na$^+$/H$^+$ exchange mechanism, be used as medicaments for the treatment of all acute or chronic ischemia-induced damage or diseases induced primarily or secondarily thereby.

This also relates to their use as medicaments for surgical interventions. Thus, the compounds can be used during organ transplantations, it being possible to use the compounds both to protect the organs in the donor before and during the removal, to protect removed organs for example during treatment with or storage thereof in physiological bath liquids, and during transference to the recipient organism.

The compounds of the invention are likewise valuable medicaments with a protective effect when performing angioplastic surgical interventions, for example on the heart as well as on peripheral organs and vessels.

It has emerged that the compounds of the invention are exceptionally effective medicaments for life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with compounds of the formula I and/or II and/or the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication with such medicaments. The therapeutic benefits of such a cytotoxic therapy can be considerably increased by combination with NHE inhibitors.

In addition, the NHE1 inhibitors of the invention of the formula I and/or II and/or the pharmaceutically acceptable salts thereof can be used when there is heart-damaging overproduction of thyroid hormones, thyrotoxicosis, or on external supply of thyroid hormones. The compounds of the formula I and/or II and/or the pharmaceutically acceptable salts thereof are thus suitable for improving therapy with cardiotoxic medicaments.

In accordance with their protective effect against ischemia-induced damage, the compounds of the invention are also suitable as medicaments for the treatment of ischemias of the nervous system, especially of the central nervous system, being suitable for example for the treatment of stroke or of cerebral edema.

The compounds of the formula I and/or II and/or the pharmaceutically acceptable salts thereof are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use the NHE inhibitors described herein alone or in combination with other substances with antiepileptic activity or antipsychotic active ingredients, or carbonate dehydratase inhibitors, for example with acetazolamide, and with other inhibitors of NHE or of the sodium-dependent chloride-bicarbonate exchanger (NCBE).

The compounds used according to the invention of the formula I and/or II and/or the pharmaceutically acceptable salts thereof are additionally likewise suitable for the treatment of types of shock such as, for example, of allergic, cardiogenic, hypovolemic and bacterial shock.

The compounds of the formula I and/or II and/or the pharmaceutically acceptable salts thereof can likewise be used for the prevention and treatment of thrombotic disorders because they, as NHE inhibitors, are able to inhibit platelet aggregation themselves. They are additionally able to inhibit or prevent the excessive release, occurring after ischemia and reperfusion, of mediators of inflammation and coagulation, especially of von Willebrand factor and of thrombogenic selectin proteins. It is thus possible to reduce and eliminate the pathogenic effect of significant thrombogenic factors. The NHE inhibitors of the present invention can therefore be combined with other anticoagulant and/or thrombolytic active ingredients such as, for example, recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonate dehydratase such as, for example, with acetazolamide, is particularly beneficial.

The compounds of the formula I and/or II and/or the pharmaceutically acceptable salts thereof used according to the invention are additionally distinguished by a strong inhibitory effect on the proliferation of cells, for example fibroblast proliferation and the proliferation of smooth vascular muscle cells. The compounds of the formula I and/or II and/or the pharmaceutically acceptable salts thereof are therefore suitable as valuable therapeutic agents for diseases in which cellular proliferation represents a primary or secondary cause, and can therefore be used as antiatherosclerotics, agents for chronic renal failure, cancers.

It was possible to show that cell migration is inhibited by the compounds of the invention. The compounds of the formula I and/or II and/or the pharmaceutically acceptable salts thereof are therefore suitable as valuable therapeutic agents for dieases in which cell migration represents a primary or secondary cause, such as, for example, cancers with a pronounced tendency to metastasis.

The compounds of the formula I and/or II and/or the pharmaceutically acceptable salts thereof are further distinguished by a retardation or prevention of fibrotic disorders. They are thus suitable as excellent agents for the treatment of cardiac fibroses, and of pulmonary fibrosis, hepatic fibrosis, renal fibrosis and other fibrotic disorders. They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of the formula I and/or II and/or the pharmaceutically acceptable salts thereof are suitable for the prevention and treatment of high blood pressure and of cardiovascular disorders.

In these cases they can be used alone or with a suitable combination and formulation partner for the treatment of high blood pressure and of cardiovascular disorders. Thus, for example, one or more diuretics with a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone, can be combined. The NHE inhibitors of the present invention can further be used in combination with calcium channel blockers such as verapamil, diltiazem, amlodipine or nifedipine, and with ACE inhibitors such as, for example, ramipril, enalapril, lisinopril, fosinopril or captopril. Further beneficial combination partners are also beta-blockers such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has emerged that NHE1 inhibitors of the formula I and/or II and/or the pharmaceutically acceptable salts thereof have a significant antiinflammatory effect and can thus be used as antiinflammatory drugs. Inhibition of the release of mediators of inflammation is noteworthy in this connection. The compounds can thus be used alone or in combination with an antiinflammatory drug for the prevention or treatment of chronic and acute inflammatory disorders. Combination partners advantageously used are steroidal and non-steroidal antiinflammatory drugs.

It has additionally been found that compounds of the formula I and/or II and/or the pharmaceutically acceptable salts thereof show a beneficial effect on serum lipoproteins. It is generally acknowledged that blood fat levels which are too high, called hyperlipoproteinemias, represent an essential risk factor for the development of arteriosclerotic vascular lesions, especially coronary heart disease. The reduction of elevated serum lipoproteins therefore has exceptional importance for the prophylaxis and regression of atherosclerotic lesions. Besides the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has now been found that NHE1 inhibitors show valuable therapeutically utilizable properties in relation to influencing the serum lipid levels. Thus, they significantly reduce the elevated serum concentrations of LDL and VLDL as are to be observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the compounds of the formula I and/or II and/or the pharmaceutically acceptable salts thereof lead to a marked reduction in the infarctions induced by metabolic abnormalities and, in particular, to a significant reduction in the induced infarct size and the severity thereof. Said compounds are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia-induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of an NHE inhibitor of the formula I and/or II and/or the pharmaceutically acceptable salts thereof with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of the formula I and/or II and/or the pharmaceutically acceptable salts thereof, proves to be a favorable combination with enhanced effect and reduced use of active ingredients.

Thus, compounds of the formula I and/or II and/or the pharmaceutically acceptable salts thereof lead to effective protection against endothelial damage of various origins. This protection of the vessels against the syndrome of endothelial dysfunction means that the compounds of the formula I and/or II and/or the pharmaceutically acceptable salts thereof are valuable medicaments for the prevention and treatment of coronary vasospasms, peripheral vascular diseases, in particular intermittent claudication, atherogenesis and atherosclerosis, left ventricular hypertrophy and dilated cardiomyopathy and thrombotic disorders.

It has additionally been found that benzoylguanidines of the formula I and/or II and/or the pharmaceutically acceptable salts thereof are suitable in the treatment of non-insulin-dependent diabetes (NIDDM), with the insulin resistance being restrained. It may in this connection be beneficial, to enhance the antidiabetic activity and quality of the effect of the compounds of the invention, to combine them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizor or with meglitinide.

Besides the acute antidiabetic effects, the compounds of the formula I and/or II and/or the pharmaceutically acceptable salts thereof counteract the development of late complications of diabetes and can therefore be used as medicaments for the prevention and treatment of late damage from diabetes, such as diabetic nephropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin should be particularly important in this connection.

The NHE inhibitors of the invention of the formula I and/or II and/or the pharmaceutically acceptable salts thereof show, besides the protective effects against acute ischemic events and the subsequent equally acutely stressing reperfusion events, also direct therapeutically utilizable effects against diseases and disorders of the entire mammalian organism which are associated with the manifestations of the chronically progressive aging process and which occur independently of acute hypoperfusion states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. The compounds of the formula I and/or II and/or the pharmaceutically acceptable salts thereof are thus outstandingly suitable for the treatment and prevention of the age-related progression in endothelial dysfunction, especially of intermittent claudication.

An example of another variable characterizing the aging process is the decline in the contractability of the heart and the decline in the adaptation of the heart to a required pumping output of the heart. This diminished efficiency of the heart as a consequence of the aging process is in most cases connected with a dysfunction of the heart which is caused inter alia by deposition of connective tissue in the myocardial tissue. This deposition of connective tissue is characterized by an increase in the weight of the heart, by an enlargement of the heart and by restrictive cardiac function. It was surprising that it was possible almost completely to inhibit such aging of the heart organ. The compounds of the formula I and/or II and/or the pharmaceutically acceptable salts thereof are thus outstandingly suitable for the treatment and prevention of heart failure, of congestive heart failure (CHF).

Whereas previous patents and patent applications have claimed the treatment of various forms of cancer which have already occurred, it was now extremely surprising that not only is it possible to cure a cancer which has already occurred through inhibition of proliferation, but there is also prevention and highly significant retardation of the age-related incidence of cancer through NHE inhibitors. A particularly noteworthy finding is that the disorders, occurring as a result of aging, of all organs and not only certain types of cancer are suppressed or occur with a highly significant delay. The compounds of the formula I and/or II and/or the pharmaceutically acceptable salts thereof are thus outstandingly suitable for the treatment and, in particular, the prevention of age-related types of cancer.

There is now found to be not only a delay, shifted highly significantly in time and beyond the normal statistical extent, in the occurrence of age-related disorders of all the organs investigated, including the heart, vessels, liver etc., and a highly significant delay in cancer of the elderly. On the contrary, there is also surprisingly a prolongation of life to an extent which has to date been achievable by no other group of medicaments or by any natural products. This unique effect of NHE inhibitors also makes it possible, besides the use of the active ingredients alone on humans and animals, to combine these NHE inhibitors with other active principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, the combination with dietary measures can take place for example with appetite suppressants. It is likewise possible to consider a combination with hypotensive medicaments such as with ACE inhiibitors, angiotensin receptor antagonists, diuretics, $Ca^{+2}$ antagonists etc. or with metabolism-normalizing medicaments such as cholesterol-lowering agents.

The compounds of the formula I and/or II and/or the pharmaceutically acceptable salts thereof are thus outstandingly suitable for the prevention of age-related tissue changes and for prolonging life while retaining a high quality of life.

The compounds of the invention are effective inhibitors of the cellular sodium-proton antiporter (Na/H exchanger) which in a large number of disorders (essential hypertension, atherosclerosis, diabetes etc.) is also increased in cells which are readily amenable to measurements, such as, for example, in erythrocytes, platelets or leucocytes. The compounds used according to the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

Also claimed is a medicine for human, veterinary or phytoprotective use, comprising an effective amount of a compound of the formula I and/or II and/or the pharmaceutically acceptable salts thereof, together with pharmaceutically acceptable carriers and additives, alone or in combination with other active pharmaceutical ingredients or medicaments.

Medicaments which comprise a compound of the formula I and/or II or the pharmaceutically acceptable salts thereof can in this connection be administered, for example, orally, parenterally, intravenously, rectally, transdermally or by inhalation, the preferred administration being dependent on the particular characteristics of the disorder. The compounds I and/or II may moreover be used alone or together with pharmaceutical excipients, both in veterinary medicine and in human medicine. The medicaments generally comprise active ingredients of the formula I and/or II or the pharmaceutically acceptable salts thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or II and/or the pharmaceutically acceptable salts thereof in a pharmaceutically acceptable solvent such as, in particular, ethanol or water, or a mixture of such solvents.

The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of the formula I and/or II to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I and/or II and/or the pharmaceutically acceptable salts thereof for a patient weighing about 75 kg is at least 0.001 mg/kg, preferably 0.01 mg/kg, to a maximum of 10 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 700 mg a day may be necessary, in particular on i.v. administration, for example for a patient with infarction in the intensive care unit, and the compounds of the invention can be administered by infusion.

List of Abbreviations:
ADMET absorption—distribution—metabolism—excretion—toxicology
CDI diimidazol-1-ylmethanone
DIP diisopropyl ether
DIPEA diisopropylethylamine
DME 1,2-dimethoxyethane
DMF N,N-dimethylformamide
EA ethyl acetate (EtOAc)
eq. equivalent
HEP n-heptane
HOAc acetic acid
KOtBu potassium 2-methylpropan-2-olate
MeOH methanol
mp melting point
MTB tert-butyl methyl ether
Pd(dppf)$_2$ [1,1'-bis-(diphenylphosphino)ferrocene]palladium(II) chloride (1:1) methylene chloride complex
RT room temperature
TFA trifluoroacetic acid
THF tetrahydrofuran
TMEDA N,N,N',N'-tetramethylethane-1,2-diamine Experimental Part

EXAMPLE 1

3-Pentafluorosulfanylbenzoylguanidine, Hydrochloride

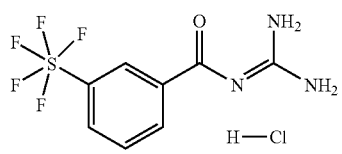

a) 3-Pentafluorosulfanylbenzoic Acid 700 mg of (3-iodophenyl)sulfur pentafluoride (Tetrahedron 56, (2000) 3399) and 300 mg of methyl iodide were dissolved in 20 ml of diethyl ether (anhydrous), and the solution was slowly added dropwise to 155 mg of magnesium/10 ml of diethyl ether. After stirring under reflux for one hour, the reaction mixture was cooled to −10° C. and $CO_2$ was passed in under atmospheric pressure. The reaction mixture was stirred at RT for 16 hours and then adjusted to pH=1 with dilute aqueous HCl solution and extracted 3 times with 50 ml of EA each time. After drying over $MgSO_4$, the solvent was removed in vacuo. Chromatography on silica gel with DIP/2% HOAc afforded 200 mg of a colorless amorphous powder.

Rf (DIP/2% HOAc)=0.51 MS (ES$^+$): 249 b) 3-Pentafluorosulfanylbenzoylguanidine, Hydrochloride 30 mg of 3-pentafluorosulfanylbenzoic acid were stirred together with 24 mg of CDI in 5 ml of DMF (anhydrous) at RT for 3 hours. Alongside, 69 mg of guanidinium chloride were stirred together with 68 mg of KOtBu in 5 ml of DMF (anhydrous) at RT for 30 minutes. The two solutions were then combined and left to stand at RT for 18 hours. The reaction mixture was diluted with 20 ml of EA and washed 3 times with 5 ml of a 50% concentrated aqueous $NaHCO_3$ solution each time. Drying over $MgSO_4$ was followed by removal of the solvent in vacuo and taking up in excess 5% aqueous HCl solution. The volatile constituents were removed in vacuo, and 33 mg of an amorphous solid were obtained.

Rf (EA)=0.30 MS (ES$^+$): 290

EXAMPLE 2

4-Pentafluorosulfanylbenzoylguanidine, Hydrochloride

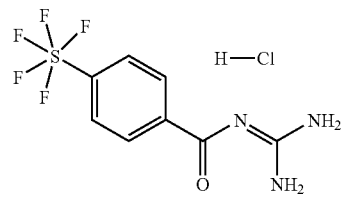

a) 4-Pentafluorosulfanylbenzoic Acid 2.7 g of (4-iodophenyl)sulfur pentafluoride (Tetrahedron 56, (2000) 3399) were reacted in analogy to example 1 a), and 630 mg of a colorless amorphous solid were obtained.

Rf (DIP/2% HOAc)=0.51 MS (ES$^+$): 249 b) 4-Pentafluorosulfanylbenzoylguanidine, Hydrochloride 50 mg of 4-pentafluorosulfanylbenzoic acid were reacted in analogy to example 1 b) and 33 mg of the title compound of example 2 were obtained as an amorphous powder.

Rf (EA)=0.30 MS (ES$^+$): 290

EXAMPLE 3

4-Pentafluorosulfanyl-2-methylbenzoylguanidine

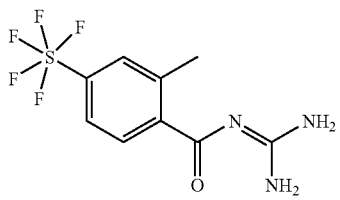

a) 4-Pentafluorosulfanyl-2-methylbenzoic Acid 3.09 g of TMEDA were dissolved in 30 ml of THF (anhydrous) and added dropwise at −90° C. to 20.5 ml of a 1.3M solution of sec-butyllithium in cyclohexane. A solution of 3.0 g of 4-pentafluorosulfanylbenzoic acid in 20 ml of THF (anhydrous) was then added dropwise at −90° C. After stirring at −90° C. for one hour, a solution of 5.15 g of methyl iodide in 20 ml of THF (anhydrous) was added dropwise. The temperature was kept at −80° C. during this. After stirring at −78° C. for 20 minutes, 100 ml of water were injected, a dilute aqueous HCl solution was used to adjust to pH=1, and the mixture was extracted 3 times with 100 ml of MTB each time. After drying over MgSO$_4$, the solvent was removed in vacuo. The residue was initially chromatographed on silica gel with DIP/2% HOAc, and 1.60 g of a mixture of 4-pentafluorosulfanylbenzoic acid and 4-pentafluorosulfanyl-2-methylbenzoic acid were obtained. This mixture was rechromatographed under the following conditions:

| column: | Waters X-terra 250 × 50 mm + precolumn 50 × 50 mm |
|---|---|
| packing: | C18 10 μM |
| flow rate: | 150 ml/min |
| gradient (linear course): | |

| solvent A | water + 2% trifluoroacetic acid | |
|---|---|---|
| solvent B | acetonitrile | |
| Time [min] | Solv. A [%] | Solv. B [%] |
| 0.00 | 90 | 10 |
| 4.00 | 90 | 10 |
| 24.00 | 25 | 75 |
| 25.00 | 5 | 95 |
| 30.00 | 5 | 95 |
| 31.00 | 90 | 10 |
| 35.00 | 90 | 10 |

900 mg of the title compound were obtained in the form of a colorless solid with a retention time of 21.14 minutes plus 360 mg of 4-pentafluorosulfanylbenzoic acid with a retention time of 20.18 minutes (detected at a wavelength of 220 nm).

R$_f$ (DIP/2% HOAc)=0.5 MS (Cl$^+$): 263; MS (ES$^-$): 261 b) 4-Pentafluorosulfanyl-2-methylbenzoylguanidine 910 mg of 4-pentafluorosulfanyl-2-methylbenzoic acid were dissolved in 25 ml of DMF (anhydrous), 844 mg of CDI were added at RT, and the mixture was stirred at RT for 6 hours (solution 1). In addition, 1.988 g of guanidinium chloride and 1.947 g of KOtBu were stirred into 10 ml of DMF (anhydrous) at RT for 30 minutes (solution 2). Solution 2 was then added to solution 1, and the reaction mixture was stirred at RT for 17 hours. It was then diluted with 200 ml of MTB and washed once with 100 ml of water. This water was then extracted with 100 ml of MTB. The combined organic phases were then washed three times more with 50 ml of water each time and dried over MgSO$_4$. The solvent was removed in vacuo and the residue was chromatographed on silica gel with EA. 600 mg of white crystals, mp 185° C., were obtained.

R$_f$ (EA)=0.22 MS (ES$^+$): 304

EXAMPLE 4

N-[2-Chloro-4-pentafluorosulfanylbenzoyl]guanidine

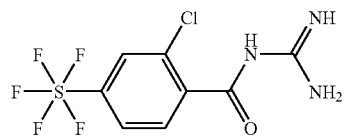

a) 2-Chloro-4-pentafluorosulfanylbenzoic Acid 20.0 ml of TMEDA were dissolved in 150 ml of THF (anhydrous) and, at a temperature between −80° C. and −90° C., 93.0 ml of a 1.25M solution of sec-BuLi in cyclohexane were added. Then, at a temperature between −87° C. and −93° C., a solution of 4-pentafluorosulfanylbenzoic acid (example 2a) in 50 ml of THF (anhydrous) was added dropwise over the course of 35 minutes, After stirring at −90° C. for 2 hours, 38.2 g of 1,1,1,2,2,2-hexachloroethane in 60 ml of THF (anhydrous) were added dropwise at −90° C. The mixture was allowed to warm to −70° C., and then 100 ml of water were added dropwise. The solvent was removed in vacuo, and the residue was chromatographed on silica gel with DIP/2% HOAc. 5.0 g of the desired product were obtained as a partly crystallizing oil.

R$_f$ (DIP/2% HOAc)=0.21 MS (EI): 282 (M+1)$^+$ b) N-[2-Chloro-4-pentafluorosulfanylbenzoyl]guanidine 170 mg of 2-chloro-4-pentafluorosulfanylbenzoic acid were dissolved in 3 ml of DMF (anhydrous) and, at RT, 127 mg of CDI were added. Stirring at RT for 2 hours resulted in the intermediate imidazolide.

Alongside, 337 mg of KOt-Bu were dissolved in 5 ml of DMF (anhydrous), and a solution of 344 mg of guanidine hydrochloride in 5 ml of DMF (anhydrous) were added dropwise. The solution was stirred at RT for 30 minutes and then a solution of the imidazolide was added dropwise at RT. The reaction mixture was left to stand at RT for 16 hours and then the solvent was removed in vacuo. The residue was taken up in 50 ml of EA/20 ml of water and washed twice with 20 ml of water each time, and then twice with 20 ml of a saturated aqueous NaCl solution each time. Drying over MgSO$_4$ was followed by removal of the solvent in vacuo. The residue was chromatographed on silica gel with EA, and 90 mg of the product (amorphous) were obtained.

R$_f$ (EA) 0.13 MS (ES+):324 (M+1)$^+$

EXAMPLE 5

N-[2-(4-Fluorophenoxy)-4-pentafluorosulfanylbenzoyl]guanidine

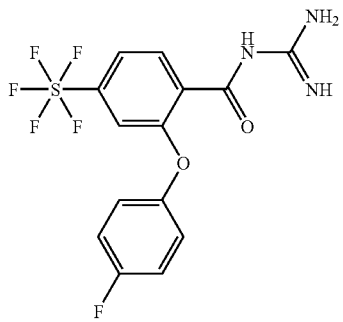

a) Methyl 2-chloro-4-pentafluorosulfanylbenzoate 4.3 g of 2-chloro-4-pentafluorosulfanylbenzoic acid were dissolved in 50 ml of methanol and, at RT, 5.6 ml of $SOCl_2$ were slowly added dropwise. After boiling under reflux for 6 hours and removal of the volatile constituents in vacuo, the residue was taken up in 100 ml of toluene, and the volatile constituents were again removed in vacuo. 4.1 g of a colorless oil were obtained.

$R_f$ (HEP/DIP 1:1)=0.44 b) Methyl 2-(4-fluorophenoxy)-4-pentafluorosulfanylbenzoate 300 mg of methyl 2-chloro-4-pentafluorosulfanylbenzoate, 113 mg of 4-fluorophenol and 659 mg of $Cs_2CO_3$ were dissolved in 1.5 ml of DMF (anhydrous) and stirred at 120° C. The mixture was then allowed to cool and was diluted with 10 ml of EA and washed 3 times with 5 ml of water each time. Drying over $MgSO_4$ was followed by removal of the solvent in vacuo. 120 mg of an amorphous solid were obtained and were chromatographed on reversed phase silica gel:

flow rate: 30 ml/min gradient: ACN=A; water+0.2% TFA=B 0-3 min 5% A;-14 min 95% A;15-18 min 95% A;-20 min 5% A column: XTerra C18 5 μm 30×100 mm 20 mg of an amorphous solid were obtained.

$R_f$ silica gel (HEP/DIP 1:1)=0.44 c) N-[2-(4-Fluorophenoxy)-4-pentafluorosulfanylbenzoyl] guanidine 270 mg of KOt-Bu and 324 mg of guanidine hydrochloride were stirred in 1 ml of DMF (anhydrous) at RT for 30 minutes. Then a solution of 54 mg of methyl 2-(4-fluorophenoxy)-4-pentafluorosulfanylbenzoate in 1 ml of DMF (anhydrous) was added. This was followed by stirring at RT for 2 hours and then pouring into 10 ml of water, adjusting to pH=8 with aqueous HCl solution and extracting 3 times with 5 ml of MTB each time. The organic phase was washed with 10 ml of water and then dried over $MgSO_4$, and finally the solvent was removed in vacuo. 20 mg of an amorphous solid were obtained.

$R_f$ (EA)=0.22 MS (ES+): 400 (M+1)$^+$

EXAMPLE 6

N-(2-Methyl-5-pentafluorosulfanylbenzoyl)guanidine

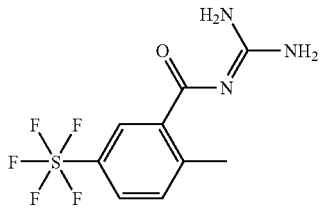

a) 1-Dichloromethyl-2-nitro-4-pentafluorosulfanylbenzene 5.4 g of KOtBu were dissolved in 25 ml of DMF (anhydrous) and 20 ml of THF (anhydrous) and cooled to −73° C. A solution of 3.0 g of 1-nitro-3-pentafluorosulfanylbenzene and 1.1 ml of $CHCl_3$ in 15 ml of DMF (anhydrous) was then added dropwise as rapidly as possible (about 20 minutes), keeping the temperature below −67° C. The mixture was stirred at −70° C. for one minute and then 15 ml of glacial acetic acid in 15 ml of methanol were injected and warmed to RT. The reaction mixture was poured into 200 ml of water and extracted 3 times with 100 ml of $CH_2Cl_2$ each time. The organic phase was then washed 3 times with 50 ml of a saturated aqueous $Na_2CO_3$ solution each time. Drying over $MgSO_4$ was followed by removal of the solvent in vacuo. The residue was chromatographed on silica gel with EA/HEP 1:10, and 3.0 g of a colorless oil were obtained.

Rf (EA/HEP 1:10)=0.78 b) 2-Methyl-5-pentafluorosulfanylaniline 2.0 g of 1-dichloromethyl-2-nitro-4-pentafluorosulfanylbenzene were dissolved in 25 ml of DME and, after addition of 200 mg of Pd/C (5%) and 100 ml of a saturated aqueous $NaHCO_3$ solution, hydrogenated under 5 bar of $H_2$ for 54 hours. The catalyst was then removed by filtration and the reaction solution was extracted 3 times with 50 ml of MTB each time. Drying over $MgSO_4$ was followed by removal of the solvent in vacuo. 1.1 g of a colorless oil were obtained.

$R_f$ (DIP)=0.42 c) 2-Bromo-1-methyl-4-pentafluorosulfanylbenzene 1.6 g of 2-methyl-5-pentafluorosulfanylaniline were dissolved in 15 ml of glacial acetic acid and, at 5° C., 3 ml of a 48% aqueous HBr solution were added dropwise. A precipitate formed during this. Then, at a temperature between 0° C. and 5° C., a solution of 0.52 g of $NaNO_2$ in 3 ml of water was added dropwise over the course of 10 minutes. This solution of the diazonium salt was then poured into a suspension of 1.2 g of CuBr in 10 ml of a 48% aqueous HBr solution and 10 ml of water. Stirring at RT for 30 minutes was followed by dilution with 50 ml of water and extraction 3 times with 50 ml of DIP each time. The organic phase was then washed twice with 50 ml of a saturated aqueous $Na_2CO_3$ solution each time. Drying over $MgSO_4$ was followed by removal of the solvent in vacuo. 1.6 g of a mobile oil were obtained.

$R_f$ (MTB/n-pentane 1:5)=0.67 d) 2-Methyl-5-pentafluorosulfanylbenzoic Acid 200 mg of 2-bromo-1-methyl-4-pentafluorosulfanylbenzene were dissolved in 6 ml of DMF, 3 ml of tri-n-butylamine and 0.5 ml of water, and 129 mg of $Cs_2CO_3$ were added. Then 15.1 mg of Pd(OAc)$_2$ and 35.3 mg of triphenylphosphine were added, and the mixture was boiled under reflux under CO under atmospheric pressure for 6 hours. The reaction mixture was diluted with 100 ml of EA and 30 ml of water, adjusted to pH=2-3 with aqueous HCl solution and extracted twice with 30 ml of EA each time. Drying over MgSO$_4$ was followed by removal of the solvent in vacuo. Reversed phase chromatography afforded 17 mg of an amorphous solid.

Chromatography methods: 3 HPLC runs; 1 run with gradient 1, 2 runs with gradient 2.

HPLC: gradient 1 and gradient 2, running time 20 min for both

Mobile phases: water (double-distilled)+0.2%.TFA, acetonitrile (Chromasolv); flow rate: 30 ml/min Column: Waters Xterra™ MS C$_{18}$ 5 μm, 30×100 mm MS: standard 20 min, fractionation: by time

| Gradient 1: | | Gradient 2: | |
|---|---|---|---|
| 0-2.5 min | 10% ACN | 0-2.5 min | 10% ACN |
| 3.0 min | 25% ACN | 3.0 min | 20% ACN |
| 14.0 min | 75% ACN | 14.0 min | 60% ACN |
| 15.0 min | 95% ACN | 15.0 min | 95% ACN |
| 17.5 min | 10% ACN | 17.5 min | 10% ACN |

LCMS (ES−): 261 (M−1)$^−$ e) N-(2-Methyl-5-pentafluorosulfanylbenzoyl)guanidine 17.0 mg of 2-methyl-5-pentafluorosulfanylbenzoic acid were dissolved in 2 ml of DMF (anhydrous) and, after addition of 15 mg of CDI, stirred at RT for 4 hours.

Alongside, 36.5 mg of KOt-Bu and 37.3 mg of Guanidine hydrochloride were dissolved in 2 ml of anhydrous DMF and stirred at RT for 30 minutes. This solution of the guanidine base was then added dropwise to the above imidazolide and left to stand at RT for 16 hours. The solvent was removed in vacuo, and the residue was taken up in 5 ml of water and adjusted to pH=9 with aqueous HCl solution. This was followed by extraction 3 times with 10 ml of EA each time. Drying over MgSO$_4$ was followed by removal of the solvent in vacuo. Chromatography on silica gel with EA afforded 7.0 mg of the product as amorphous solid.

R$_f$ (EA)=0.20 MS(ES+): 304 (M+1)$^+$

NHE Inhibition Method

The NHE-1 inhibition IC$_{50}$ [nM] was determined as follows:

FLIPR assay for determining NHE-1 inhibitors by measurement of the recovery in pH$_i$ in transfected cell lines which express human NHE-1

The assay is carried out in an FLIPR (fluorometric imaging plate reader) with black-walled 96-well microtiter plates with clear bases. The transfected cell lines expressing the various NHE subtypes (the parental cell line LAP-1 shows no endogenous NHE activity as a result of mutagenesis and subsequent selection) are seeded the preceding day at a density of ~25 000 cells/well. [The growth medium for the transfected cells (Iscove+10% fetal calf serum) additionally contains G418 as selection antibiotic in order to ensure the presence of the transfected sequences.]

The actual assay starts with the removal of the growth medium and addition of 100 μl of loading buffer per well (5 μM BCECF-AM [2',7'-bis(carboxyethyl)-5- (and -6-)carboxyfluorescein, acetoxymethyl ester] in 20 mM NH$_4$Cl, 115 mM choline chloride, 1 mM MgCl$_2$, 1 mM CaCl$_2$, 5 mM KCl, 20 mM HEPES, 5 mM glucose; pH 7.4 [adjusted with KOH]). The cells are then incubated at 37° C. for 20 minutes. This incubation leads to loading of the cells with the fluorescent dye whose fluorescence intensity depends on pHi, and with NH$_4$Cl which makes the cells slightly alkaline. [The nonfluorescent dye precursor BCECF-AM is, as ester, membrane-permeable. The actual dye BCECF is not membrane-permeable but is liberated inside cells by esterases.]

After this incubation for 20 minutes, the loading buffer which contains NH$_4$Cl and free BCECF-AM is removed by washing three times in a cell washer (Tecan Columbus) with in each case 400 μl of washing buffer (133.8 mM choline chloride, 4.7 mM KCl, 1.25 mM MgCl$_2$, 1.25 mM CaCl$_2$, 0.97 mM K$_2$HPO$_4$, 0.23 mM KH$_2$PO$_4$, 5 mM HEPES, 5 mM glucose; pH 7.4 [adjusted with KOH]). The residual volume remaining in the wells is 90 μl (50-125 μl possible). This washing step removes the free BCECF-AM and results, as a consequence of the removal of the external NH$_4^+$ ions, in intracellular acidification (~pH$_i$ 6.3-6.4).

Since the equilibrium of intracellular NH$_4^+$ with NH$_3$ and H$^+$ is disturbed by the removal of the extracellular NH$_4^+$ and by the subsequent instantaneous passage of the NH$_3$ through the cell membrane, the washing process results in H$^+$ remaining inside the cells, which is the cause of the intracellular acidification. This may eventually lead to cell death if it persists long enough.

It is important at this point that the washing buffer is sodium-free (<1 mM) because extracellular sodium ions would lead to an instantaneous recovery of the pH$_i$ through the activity of the cloned NHE isoforms.

It is likewise important for all the buffers used (loading buffer, washing buffer, recovery buffer) not to contain any HCO$_3$-ions, because the presence of bicarbonate would lead to activation of interfering bicarbonate-dependent pH$_i$ regulatory systems present in the parental LAP-1 cell line.

The microtiter plates with the acidified cells are then (up to 20 minutes after the acidification) transferred to the FLIPR. In the FLIPR, the intracellular fluorescent dye is excited by light with a wavelength of 488 nm generated by an argon laser, and the measured parameters (laser power, illumination time and aperture of the CCD camera incorporated in the FLIPR) are chosen so that the average fluorescence signal per well is between 30 000 and 35 000 relative fluorescence units.

The actual measurement in the FLIPR starts with a photograph being taken by the CCD camera every two seconds under software control. After ten seconds, the recovery of the intracellular pH is initiated by adding 90 μl of recovery buffer (133.8 mM NaCl, 4.7 mM KCl, 1.25 mM MgCl$_2$, 1.25 mM CaCl$_2$, 0.97 mM K$_2$HPO$_4$, 0.23 mM KH$_2$PO$_4$, 10 mM HEPES, 5 mM glucose; pH 7.4 [adjusted with NaOH]) by means of the 96-well pipettor incorporated in the FLIPR.

Positive control wells (100% NHE activity) are those to which pure recovery buffer is added, while negative controls (0% NHE activity) receive washing buffer. Recovery buffer with twice the concentration of test substance is added to all the other wells. Measurement in the FLIPR terminates after 60 measurements (two minutes).

The raw data are exported into the ActivityBase program. This program firstly calculates the NHE activities for each tested substance concentration and, from these, the IC$_{50}$ values for the substances. Since the progress of pH$_i$ recovery is not linear throughout the experiment, but falls at the end owing to decreasing NHE activity at higher pH$_i$ values, it is important to select for evaluation of the measurement the part in which the increase in fluorescence of the positive controls is linear.

| Example | NHE1 inhibition IC$_{50}$ [nM] |
|---|---|
| 1 | 237 |
| 2 | 131 |
| 3 | 14.5 |
| 4 | 220 |
| 5 | 12000 |
| 6 | 20.3 |

What is claimed is:
1. A pentafluorosulfanylbenzoylguanidine compound of the formula I or II

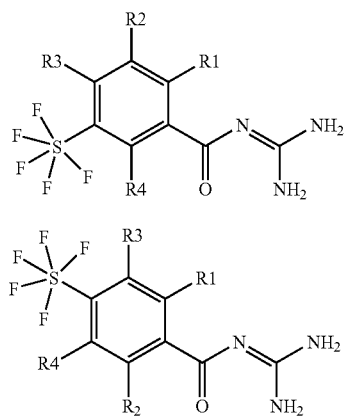

in which
R1 is hydrogen, alkyl having 1, 2, 3 or 4 carbon atoms, alkoxy having 1, 2, 3 or 4 carbon atoms, F, Cl, Br, I, CN, NR10R11, —O$_p$—(CH$_2$)$_n$—(CF$_2$)$_o$—CF$_3$ or —(SO$_m$)$_q$—(CH$_2$)$_r$—(CF$_2$)$_s$—CF$_3$;
R10 and R11 are, independently of one another, hydrogen, alkyl having 1, 2, 3 or 4 carbon atoms or —CH$_2$—CF$_3$;
m is zero, 1 or 2
n, o, p, q, r and s are, independently of one another, zero or 1;
R2 is hydrogen, F, Cl, Br, I, —CN, —SO$_2$CH$_3$, —(SO$_h$)$_z$—(CH$_2$)$_k$—(CF$_2$)$_l$—CF$_3$, alkyl having 1, 2, 3, 4, 5 or 6 carbon atoms, or cycloalkyl having 3, 4, 5, 6, 7 or 8 carbon atoms, in which 1, 2, 3 or 4 hydrogen atoms may be replaced by fluorine atoms;
h is zero, 1 or 2;
z is zero or 1;
k is zero, 1, 2, 3 or 4;
l is zero or 1; or
R2 is —(CH$_2$)$_t$-phenyl or —O-phenyl,
in which each phenol is unsubstituted or substituted by 1, 2 or 3 radicals selected from the group consisting of F, Cl, Br, I, —O$_u$—(CH$_2$)$_v$—CF$_3$, alkoxy having 1, 2, 3 or 4 carbon atoms, alkyl having 1, 2, 3 and or 4 carbon atoms and —SO$_2$CH$_3$;
t is zero, 1, 2, 3 or 4;
u is zero or 1;
v is zero, 1, 2 or 3;
or
R2 is —(CH$_2$)$_w$-heteroaryl, in which heteroaryl is unsubstituted or substituted by 1, 2 or 3 radicals selected from the group consisting of F, Cl, Br, I, —O$_x$—(CH$_2$)$_y$—CF$_3$, alkoxy having 1, 2, 3 or 4 carbon atoms, alkyl having 1, 2, 3 or 4 carbon atoms and —SO$_2$CH$_3$;
w is zero, 1, 2, 3 or 4;
x is zero or 1;
y is zero, 1, 2 or 3; and
R3 and R4 are, independently of one another, hydrogen or F;
or a pharmaceutically acceptable salt thereof.
2. The compound of the formula I or II as claimed in claim 1, wherein:
R1 is hydrogen, alkyl having 1, 2, 3 or 4 carbon atoms, alkoxy having 1, 2, 3 or 4 carbon atoms, F, Cl, NR10R11, —O—CH$_2$—CF$_3$ or SO$_m$(CH$_2$)$_r$—CF$_3$;
R10 and R11 are independently of one another hydrogen, alkyl having 1, 2, 3 or 4 carbon atoms or —CH$_2$—CF$_3$;
m is zero, 1 or 2;
r is zero or 1;
R2 is hydrogen, F, Cl, —SO$_2$CH$_3$, —(SO$_h$)$_z$—(CH$_2$)$_k$—CF$_3$, alkyl having 1, 2, 3 or 4 carbon atoms, or cycloalkyl having 3, 4, 5, 6 or 7 carbon atoms, in which 1, 2, 3 or 4 hydrogen atoms may be replaced by fluorine atoms;
h is zero, 1 or 2;
z is zero or 1;
k is zero, 1, 2, 3 or 4;
or
R2 is phenyl or —O-phenyl, which is unsubstituted or substituted by 1 or 2 radicals selected from the group consisting of F, Cl, —O$_u$—(CH$_2$)$_v$—CF$_3$, methoxy, ethoxy, alkyl having 1, 2, 3 or 4 carbon atoms and —SO$_2$CH$_3$;
u is zero or 1;
v is zero, 1, 2 or 3;
or
R2 is heteroaryl, which is unsubstituted or substituted by 1 or 2 radicals selected from the group consisting of F, Cl, —O$_x$—(CH$_2$)$_y$—CF$_3$, methoxy, ethoxy, alkyl having 1, 2, 3 or 4 carbon atoms and —SO$_2$CH$_3$;
x is zero or 1;
y is zero, 1, 2 or 3; and
R3 and R4 are independently of one another hydrogen or F;
or a pharmaceutically acceptable salt thereof.
3. The compound of the formula I or II as claimed in claim 2, wherein:
R1 is hydrogen, alkyl having 1, 2, 3 or 4 carbon atoms, methoxy, ethoxy, F, Cl, NR10R11, —O—CH$_2$—CF$_3$ or —SO$_m$—(CH$_2$)$_r$—CF$_3$;
R10 and R11 independently of one another hydrogen, alkyl having 1, 2, 3 or 4 carbon atoms or —CH$_2$—CF$_3$;
m is zero, 1 or 2;
r is zero or 1;
R2 is hydrogen, F, Cl, —SO$_2$CH$_3$, —(SO$_h$)$_z$—(CH$_2$)$_k$—CF$_3$, alkyl having 1, 2, 3 or 4 carbon atoms, or cycloalkyl having 3, 4, 5, 6 or 7 carbon atoms, in which 1, 2, 3 or 4 hydrogen atoms may be replaced by fluorine atoms;
h is zero or 2;
z is zero or 1;
k is zero or 1;
or R2 is phenyl or —O-phenyl, which is unsubstituted or substituted by 1 or 2 radicals selected from the group consisting of F, Cl, —O—(CH$_2$)$_v$—CF$_3$, methoxy, ethoxy, alkyl having 1, 2, 3 or 4 carbon atoms and —SO$_2$CH$_3$;

v is zero, 1, 2 or 3;

or

R2 is heteroaryl, which is unsubstituted or substituted by 1 or 2 radicals selected from the group consisting of F, Cl, —O—(CH$_2$)$_y$—CF$_3$, methoxy, ethoxy, alkyl having 1, 2, 3 or 4 carbon atoms and —SO$_2$CH$_3$;

y is zero, 1, 2 or 3; and

R3 and R4 are hydrogen;

or a pharmaceutically acceptable salt thereof.

* * * * *